US011041590B2

(12) United States Patent
Virovets et al.

(10) Patent No.: US 11,041,590 B2
(45) Date of Patent: Jun. 22, 2021

(54) APPARATUS FOR FILLING PRESSURIZED GAS CARTRIDGES FOR MEDICAL USE (71) Applicant: Airgas, Inc., Radnor, PA (US)

(72) Inventors: Alexey Virovets, Sandy Hook, CT (US); Robert F. Shock, Wallingford, CT (US); Celina Gwizdala, East Hampton, CT (US); Peter G. Sandberg, Warren, CT (US); James L. Gruenbacher, Southington, CT (US); David D. Brengel, Farmington, CT (US); Thomas Costello, Upper Black Eddy, PA (US); Bimesh Neupane, Cheshire, CT (US)

(73) Assignee: Airgas, Inc., Radnor, PA (US)

( * ) Notice: Subject to any disclaimer, the term of this patent is extended or adjusted under 35 U.S.C. 154(b) by 208 days.

(21) Appl. No.: 16/267,505

(22) Filed: Feb. 5, 2019

(65) Prior Publication Data
US 2019/0240693 A1 Aug. 8, 2019

Related U.S. Application Data (60) Provisional application No. 62/626,250, filed on Feb. 5, 2018.

(51) Int. Cl.
*F17C 5/06* (2006.01)
*A61M 5/24* (2006.01)
(Continued)

(52) U.S. Cl.
CPC .................. *F17C 5/06* (2013.01); *A61M 5/24* (2013.01); *B05B 7/2421* (2013.01);
(Continued)

(58) Field of Classification Search
CPC .. F17C 5/002; F17C 5/007; F17C 5/06; F17C 2270/02
(Continued)

(56) References Cited

U.S. PATENT DOCUMENTS 1,790,787 A * 2/1931 Badger ................ B23K 11/002
53/83
2,417,361 A * 3/1947 Herzog .................... H01J 5/42
141/66
(Continued)

FOREIGN PATENT DOCUMENTS

EP 0 947 760 10/1999
FR 2645620 A1 * 10/1990 .............. F17C 5/005
(Continued)

OTHER PUBLICATIONS

International Search Report and Written Opinion for corresponding PCT/US2019/016574, dated Apr. 23, 2019.

*Primary Examiner* — Stephen F. Gerrity
(74) *Attorney, Agent, or Firm* — Elwood L. Haynes (57) ABSTRACT An apparatus for filling a cartridge with medical gas, comprising a sealing mechanism designed to removably seal against the open end of an uncapped and empty cartridge, evacuate the cartridge, producing at least a partial vacuum therein, fill the cartridge with medical gas at a predetermined pressure and temperature, and maintain the predetermined pressure and temperature while the cartridge is capped is presented.

12 Claims, 10 Drawing Sheets (51) Int. Cl.
  *B05B 7/24* (2006.01)
  *B05C 17/005* (2006.01)
  *A61M 11/08* (2006.01)
  *A61M 15/00* (2006.01)
  *A61B 18/00* (2006.01)
  *B05B 1/30* (2006.01)

(52) U.S. Cl.
  CPC .. *B05C 17/005* (2013.01); *A61B 2018/00017* (2013.01); *A61B 2018/00577* (2013.01); *A61M 11/08* (2013.01); *A61M 15/009* (2013.01); *A61M 2202/0208* (2013.01); *A61M 2207/00* (2013.01); *B05B 1/3026* (2013.01)

(58) Field of Classification Search
  USPC ........... 53/403, 405, 408, 79–86, 88, 89, 94; 141/8, 66
  See application file for complete search history.

(56) References Cited

U.S. PATENT DOCUMENTS

| | | | | |
|---|---|---|---|---|
| 2,532,315 A * | 12/1950 | Johnson et al. | ........ | H01J 29/94 53/88 |
| 2,685,383 A * | 8/1954 | Kochner | ................ | F17C 13/06 220/583 |
| 3,212,228 A | 10/1965 | Merz | | |
| 3,440,797 A * | 4/1969 | Spielmann | ................ | F17C 5/06 53/83 |
| 3,924,382 A * | 12/1975 | Overkott | ................... | F17C 5/06 53/403 |
| 4,012,271 A * | 3/1977 | Brummett et al. | ..... | B65B 53/02 156/423 |
| 5,029,730 A * | 7/1991 | Kostecki et al. | ......... | F17C 5/06 222/3 |
| 5,760,360 A * | 6/1998 | Richardson, Jr. et al. | .................. | F17C 5/06 219/50 |
| 5,829,223 A * | 11/1998 | Tobin | ........................ | F17C 5/06 53/80 |
| 6,109,004 A * | 8/2000 | Bauer | ....................... | F17C 5/06 53/408 |
| 6,214,282 B1 * | 4/2001 | Katou et al. | ............ | B65B 3/022 264/163 |
| 2006/0260710 A1 * | 11/2006 | Barrett | .................... | F17C 13/06 141/17 |
| 2013/0213521 A1 | 8/2013 | Isom et al. | | |
| 2015/0375884 A1 * | 12/2015 | Kelley | ...................... | B67C 3/14 53/440 |
| 2016/0284153 A1 * | 9/2016 | Tansey, Jr. et al. | ....... | B65B 3/04 |

FOREIGN PATENT DOCUMENTS

JP        2004 197783      7/2004
WO    WO 00 31460      6/2000

\* cited by examiner

APPARATUS FOR FILLING PRESSURIZED GAS CARTRIDGES FOR MEDICAL USE

CROSS REFERENCE TO RELATED APPLICATIONS

This application claims the benefit of priority to U.S. Patent Application No. 62/626,250, filed Feb. 5, 2018, the entire contents of which are incorporated herein by reference.

BACKGROUND

Portable medical gas delivery systems typically utilize a compressed gas supply in the form of small, disposable cartridges.

SUMMARY

An apparatus for filling a cartridge with medical gas, comprising a sealing mechanism designed to removably seal against the open end of an uncapped and empty cartridge, evacuate the cartridge, producing at least a partial vacuum therein, fill the cartridge with medical gas at a predetermined pressure and temperature, and maintain the predetermined pressure and temperature while the cartridge is capped is presented.

An apparatus for filling a cartridge with medical gas including a sealing mechanism configured to removably seal against the open end of an uncapped and empty cartridge, an evacuation adapter fluidically attached to the sealing mechanism and configured to evacuate the cartridge, producing at least a partial vacuum therein, a fill adapter fluidically attached to the sealing mechanism and configured to fill the cartridge with medical gas at a predetermined pressure and temperature, and a capping device fluidically attached to the sealing mechanism and configured to maintain the predetermined pressure and temperature while the cartridge is capped is presented.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DETAILED DESCRIPTION OF THE PREFERRED EMBODIMENTS

Element Numbers

101=cartridge
102=support cradle/water cooled electrode
103=enclosed area
104=evacuation/filling adaptor
105=evacuation circuit block valve
106=vacuum pump
107=vent
108=filling circuit block valve
109=medical gas source
110=sealing member
111=capping and welding device
112=centering member
113=welding mechanism
114=cartridge cap
115=electrode
116=welding and filling adaptor
117=enclosure vent
118=centering member adjustment
119=safety enclosure
120=oven
121=water cooling passage
122=cool water inlet
123=warm water outlet
124=scale
125=optical system Illustrative embodiments of the invention are described below. While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

According to the Food and Drug Administration Compliance Program Guidance Manual for Compressed Medical Gases (Implementation date of Mar. 15, 2015), a "designated medical gas" is defined to include oxygen, nitrogen, nitrous oxide, carbon dioxide, helium, carbon monoxide, medial air, and mixtures thereof. As used herein, the term medical gas may also include argon and xenon. The term medical gas may also include any gas that has FDA or equivalent regulatory body drug approval.

One aspect of this invention are pharmacopeia gases in cartridges for at least the following list of indications:
- Skin ablation
- Endometrial ablation
- Transdermal gas delivery for Ischemia
- Transdermal gas delivery for muscle recovery after exercise
- Wound care
- Cardiac ablation
- Peripheral angiography
- Sclerotherapy
- Inhalation delivery of bronchodilators One embodiment of the present invention covers filling cartridges with all "medical and pharmaceutical gases" herein defined as:
- Designated pharmacopeia gases,
- Medical device gases,
- Active Pharmaceutical Ingredient (API) gases,
- Final Pharmaceutical (drug) gases or
- Any gas that is regulated by the US Food and Drug Agency (FDA) or an equivalent regulatory body in any other country or jurisdiction The basic inventive process may be understood as comprising six basic steps, which will be described in more detail below. These six basic steps may be understood to be an initialization step, wherein the cartridge 101 to be filled is loaded into the apparatus and placed in position. When in position, the second basic step of evacuating the cartridge of air is performed. After evacuation, third basic step of filling the cartridge with the desired medical, pharmaceutical, or pharmacopeia gas is performed. In the fourth step, the filled cartridge relocated (if necessary) to be properly positioned for the fifth step. The fifth step is the capping of the filled cartridge. The sixth and final step is the unloading of the filled cartridge from the apparatus.

It will be understood that these basic steps are presented in order to better understand the invention, but additional intermediate steps may be performed, one or more of these steps may be performed concurrently, and one or more of these steps may be bypassed while maintaining the basic operation of this invention.

Figure 1:
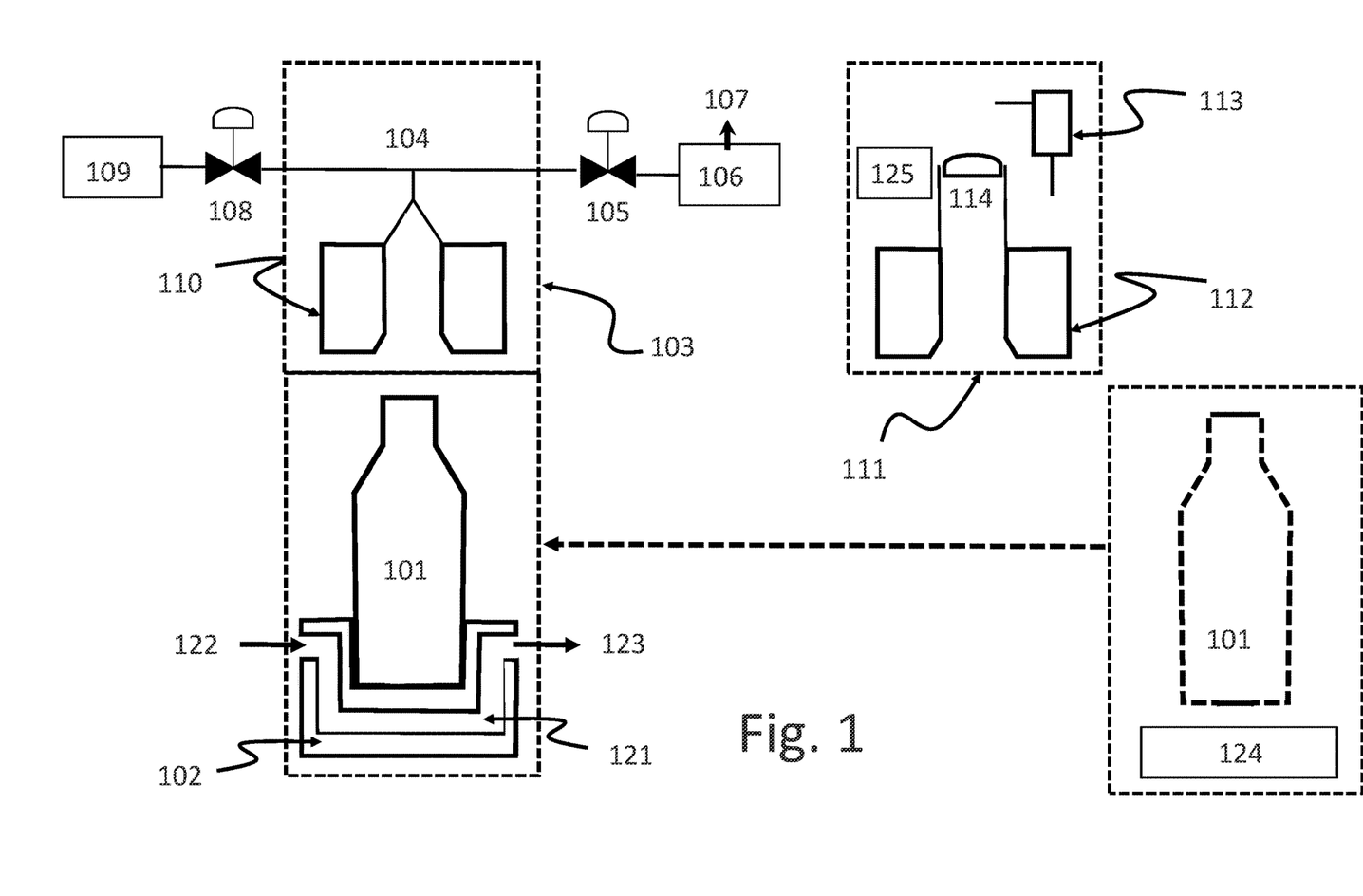
FIG. 1 is a schematic representation of the overall system during the initialization phase, in accordance with one embodiment of the present invention.

Turning now to FIG. 1, a basic schematic representation of the overall system during the initial step is illustrated. Cartridge 101 may be made from steel. In one embodiment, cartridge 101 may be made of a medical grade carbon steel alloy steel (DC04 for example). In another embodiment, cartridge 101 may be made from stainless steel. Common sizes for cartridge 101 range from about 8 g to about 88 g, with cartridges between about 20 g and 40 g being typical. A cartridge size of between 16 g and 25 g is preferred. More preferred is a cartridge size of 16 g.

The volume of cartridge 101 may be between about 15 ml and about 180 ml. The volume may be between 30 ml and 160 ml. The volume may be between 35 ml and 70 ml.

One aspect of this invention is an apparatus for filling and capping a medical grade cartridge with medical grade gas, which includes a support cradle 102 into which an uncapped and empty cartridge 101 is placed. In some embodiments, cartridge 101 is loaded outside of an enclosed area 103, then moves into enclosed area 103 wherein it is placed into support cradle 102.

During the filling step (below), as the medical grade gas is introduced into cartridge 101, the heat of compression can cause the temperature of cartridge 101 to rise considerably. For example, if pure carbon dioxide is adiabatically compressed from 25 C and one atmosphere of pressure, to 800 psig, the resulting compressed gas would have a theoretical temperature of 490 C. And, likewise, if this gas is adiabatically compressed to 2000 psig, the resulting compressed gas would have a theoretical temperature of 630 C. These temperatures can present metallurgical problems for cartridge 101. Therefore, as will be discussed below, support cradle 102 may also function as a water-cooled electrode, that will be used during the capping and welding step. In one embodiment, cool water enters in inlet 122, passes through water cooling passages 121, and the warmed water exits outlet 123. The present invention is design so that the pressure in cartridge 101 will not exceed 4,000 psia at 70 C, thus providing a much higher degree of safety.

Within the enclosed area is an evacuation and filling adaptor 104. Evacuation and filling adaptor 104 includes at least an evacuation circuit and a filling circuit. In some embodiments the evacuation and filling device 104 and a capping and welding device 111 (discussed below) are incorporated into a common device 116. The evacuation circuit includes at least a block valve 105, a vacuum pump 106, and a vent 107. The filling circuit includes at least a block valve 108, and a medical gas source 109. The evacuation and filling adaptor 104 also includes a sealing member 110 that is fluidically connected to both the evacuation circuit and the filling circuit, and is configured to sealably and removably attach and detach from cartridge 101.

Figure 2:
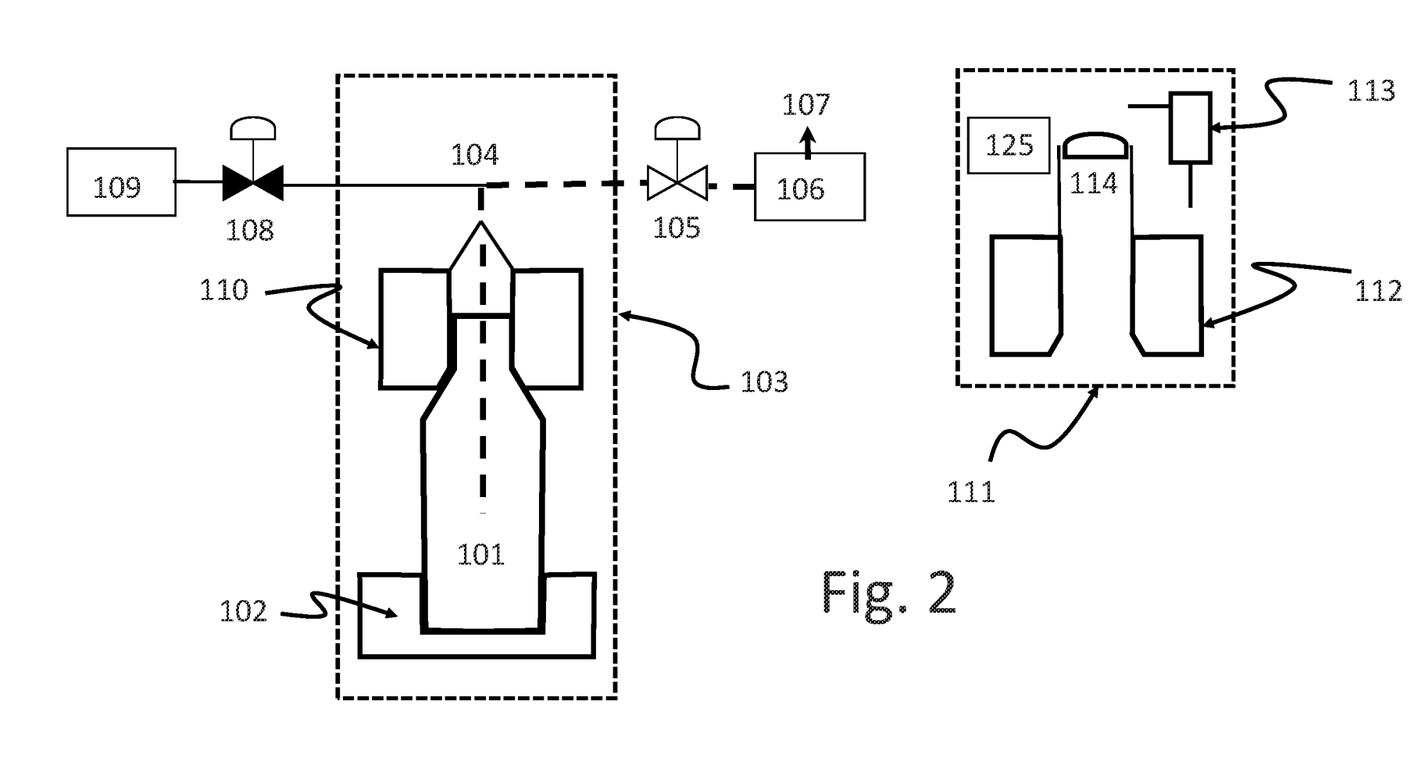
FIG. 2 is a schematic representation of the overall system during the evacuation phase, in accordance with one embodiment of the present invention.

Turning now to FIG. 2, once uncapped and empty cartridge 101 moves into enclosed area 103, sealing member 110 is sealably attached to the top of cartridge 101. In some embodiments sealing member 110 lowers onto cartridge 101. In some embodiments cartridge 101 is raised to contact sealing member 110. In some embodiments, optical system 125 may be employed to ensure that the cap us present and/or that the cartridge is properly located and aligned.

With filling circuit block valve 108 closed, and evacuation circuit block valve 105 open, vacuum pump 106 is activated. Evacuation and filling adaptor 104 then removes the existing, residual, ambient air that is contained within cartridge 101, venting the evacuated air through vent 107, and thus creating at least a partial vacuum therein.

Figure 3:
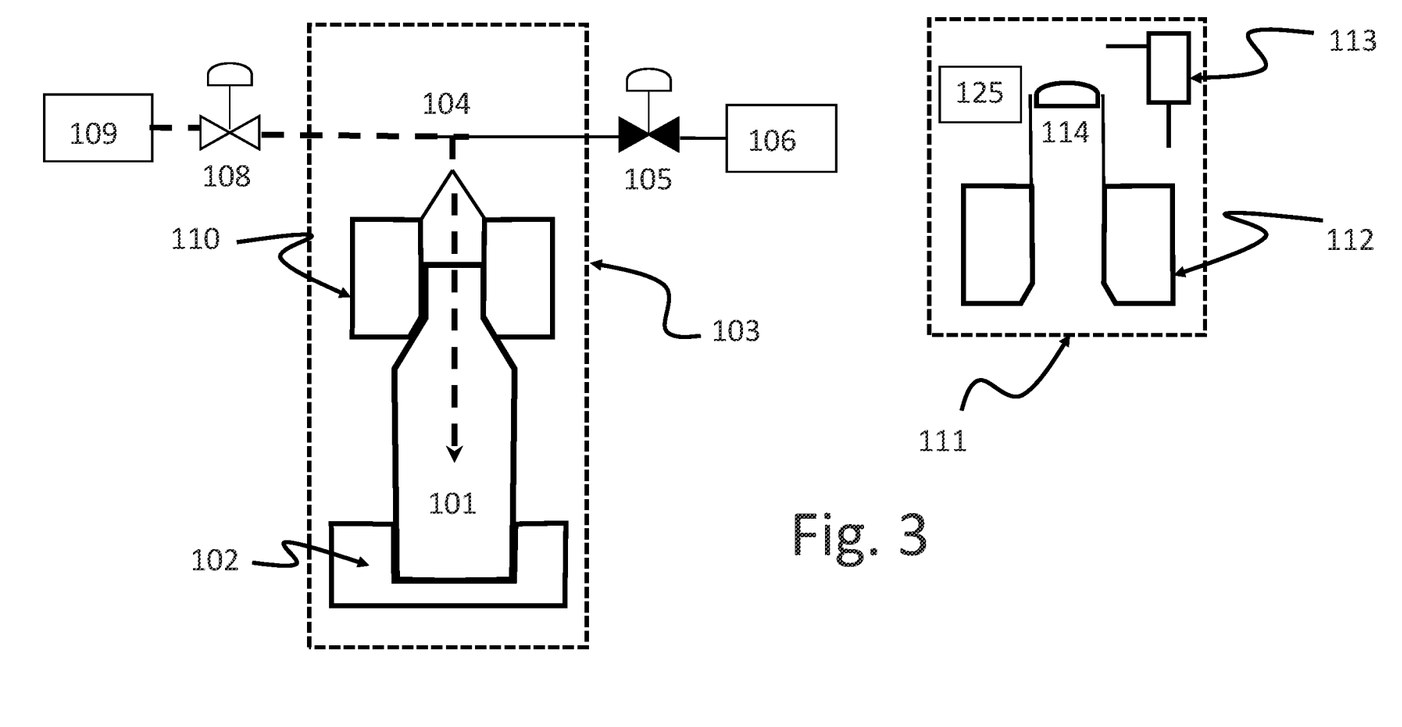
FIG. 3 is a schematic representation of the overall system during the filling phase, in accordance with one embodiment of the present invention.

Turning now to FIG. 3, once the ambient air has been evacuated from the cartridge, evacuation and filling adaptor 104 then provides medical, pharmacopeia, or pharmaceutical grade gas (as defined above) from source 109 at a predetermined pressure and temperature.

As used herein, the term "predetermined temperature" is defined as roughly ambient temperature. The "predetermined temperature" may be between 20 and 35 C, preferably between 25 and 28 C".

As used herein, the term "predetermined pressure" may be between 800 and 2000 psi, preferably between 1200 and 1500 psi (at the above predetermined temperature)

Now, with filling circuit block valve 108 open, and evacuation circuit block valve 105 closed, medical gas from source 109 is allowed to enter cartridge 101, replacing the vacuum and pressurizing the cartridge. The predetermined pressure and temperature of the gas determines the density of the gas, which, given the known volume of cartridge 101, allows a predetermined mass of medical gas present in cartridge 101.

Figure 8:
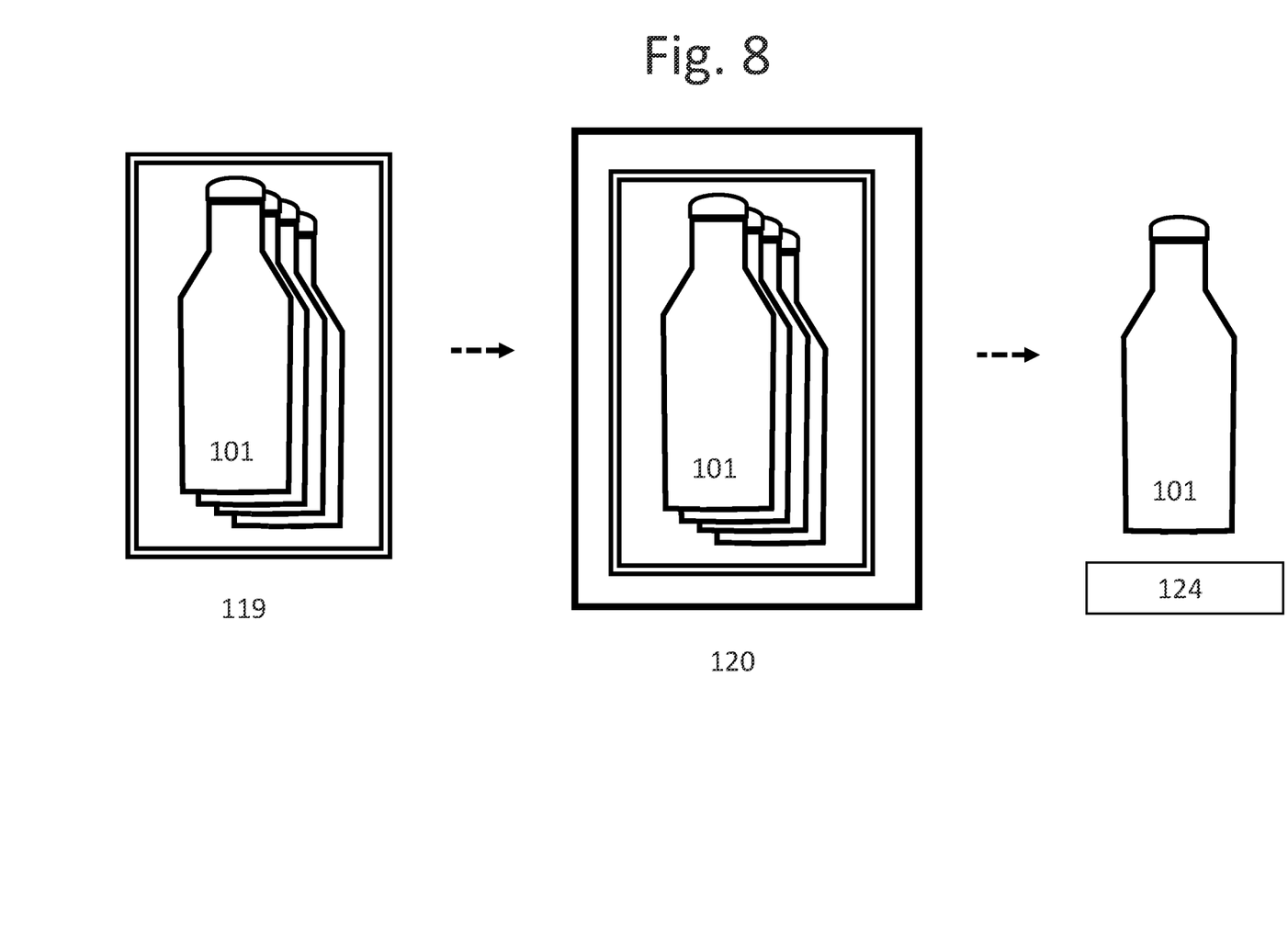
FIG. 8 is a schematic representation of the overall system during the post treatment phase, in accordance with one embodiment of the present invention.

This procedure thus eliminates the need for weighing cartridge 101 either before filling, during filling, or after filling as the mass of the medical gas is known. However, in one embodiment, as indicated in FIG. 1, cartridge 101 may be weighed on scale 124 prior to filling. And then, as indicated in FIG. 8, cartridge 101 may be weighted again on scale 124 after filling. This may be done randomly in order to calibrate or validate the above system.

Figure 4:
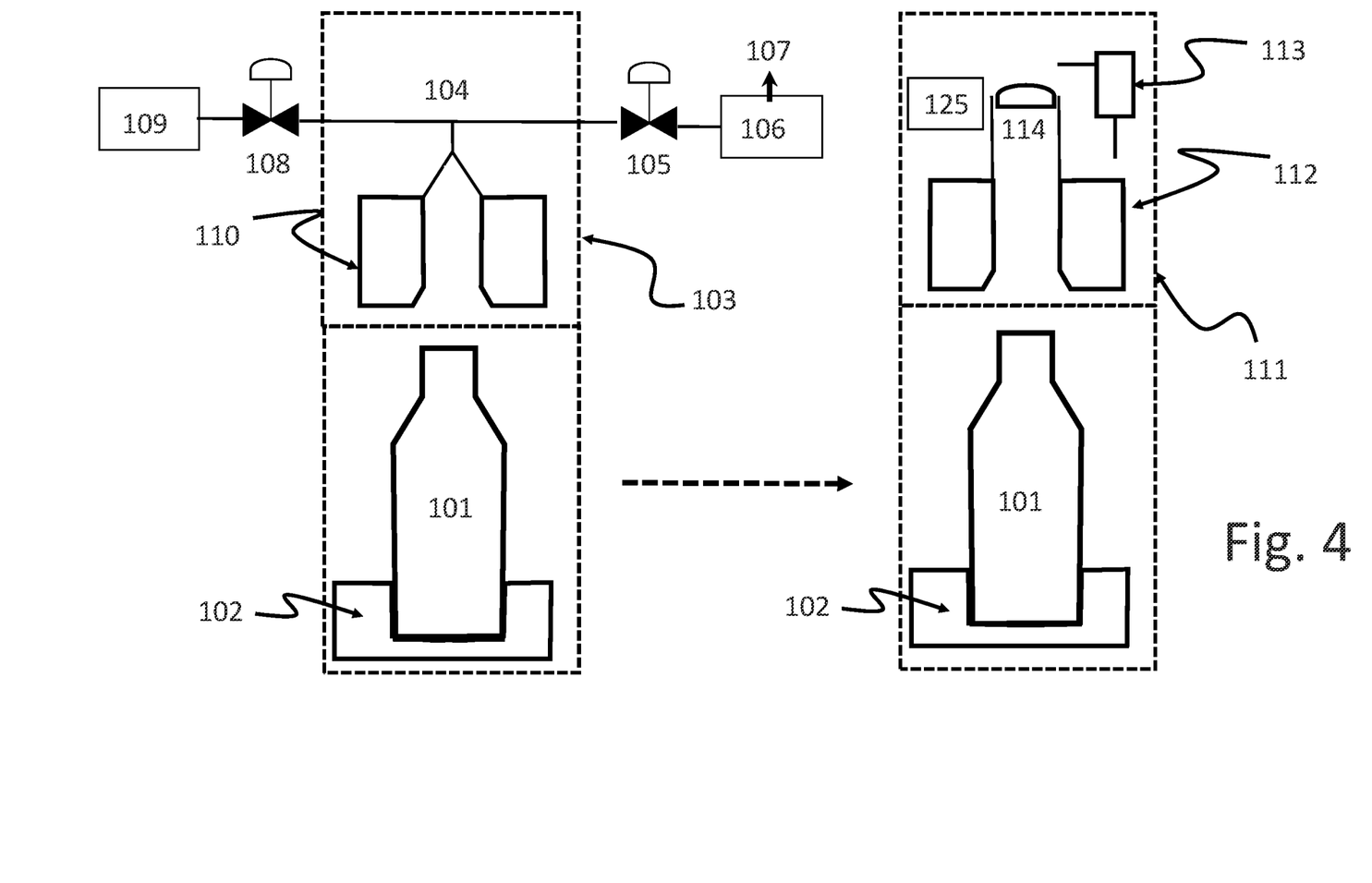
FIG. 4 is a schematic representation of the overall system during the repositioning phase, in accordance with one embodiment of the present invention.

Turning now to FIG. 4, while maintaining the medical grade gas at the predetermined pressure and temperature, support cradle 102 is repositioned (if necessary) to allow access to the capping and welding device 111. Capping and welding device 111 includes a centering member 112 for centering cartridge 101, and a welding mechanism 113. As mentioned above, in some embodiments the evacuation and filling device 104 and the capping and welding device 111 are incorporated into a common device 116, and in this case this repositioning step may not be needed.

Figure 5:
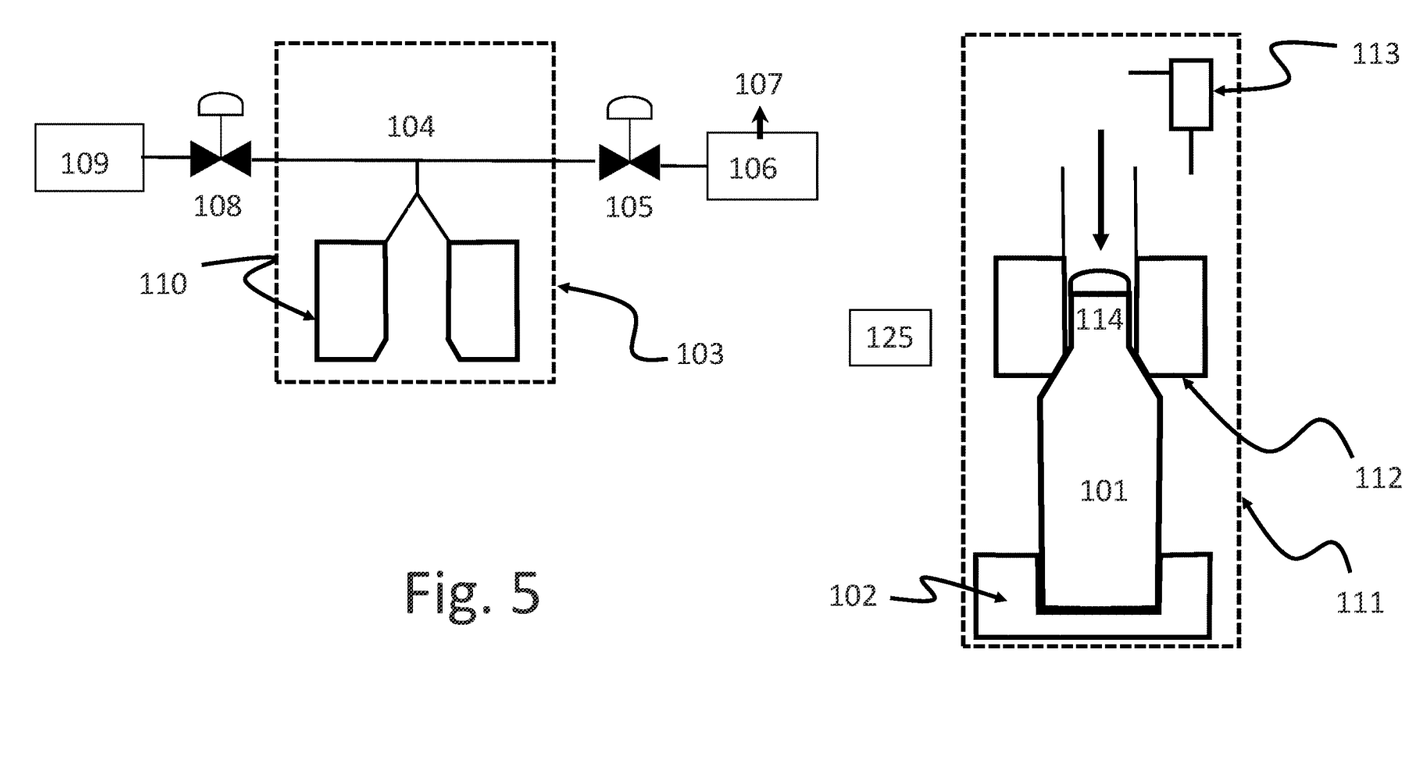
FIG. 5 is a schematic representation of the overall system during the capping phase, in accordance with one embodiment of the present invention.

Turning now to FIG. 5, capping and welding device 111 firmly attaches a cap 114 to the open end of cartridge 101. Again, in some embodiments the evacuation and filling device 104 and the capping and welding device 111 are incorporated into a common device 116. In some embodiments capping and welding device 111 lowers onto cartridge 101. In some embodiments cartridge 101 is raised to contact capping and welding device 111. Capping and welding device 111 then affixes cap 114 to cartridge 101. In some embodiments, optical system 125 may be employed to ensure that the cap and cartridge have aligned properly, and the resulting cap shape is correct.

Figure 6:
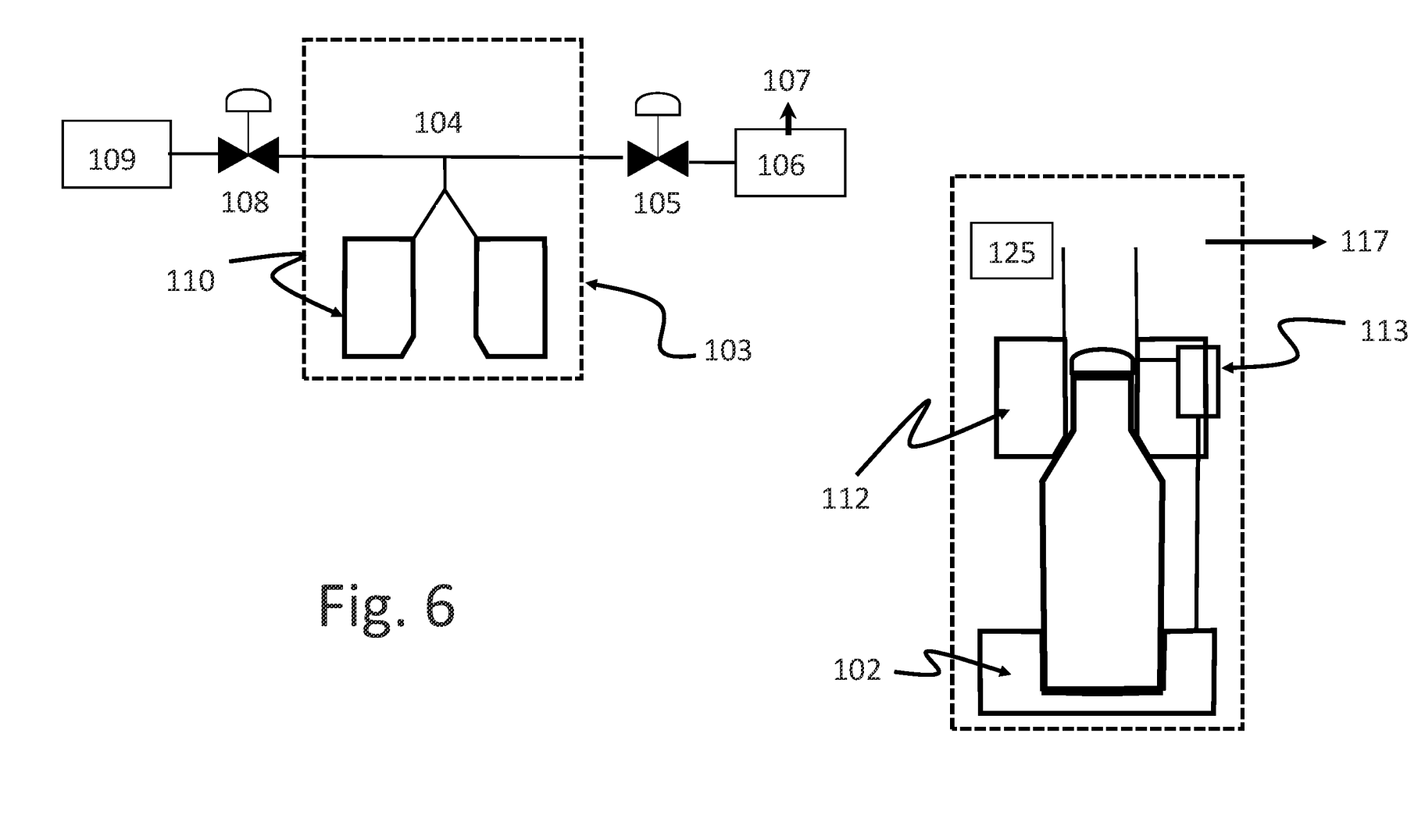
FIG. 6 is a schematic representation of the overall system during the welding phase, in accordance with one embodiment of the present invention.

Turning now to FIG. 6, in one embodiment, cap 101 is permanently affixed to cartridge 101 by means of a welding mechanism 113. Any pressurized medical gas that remains in the evacuation and filling adaptor is now vented 117.

Figure 7:
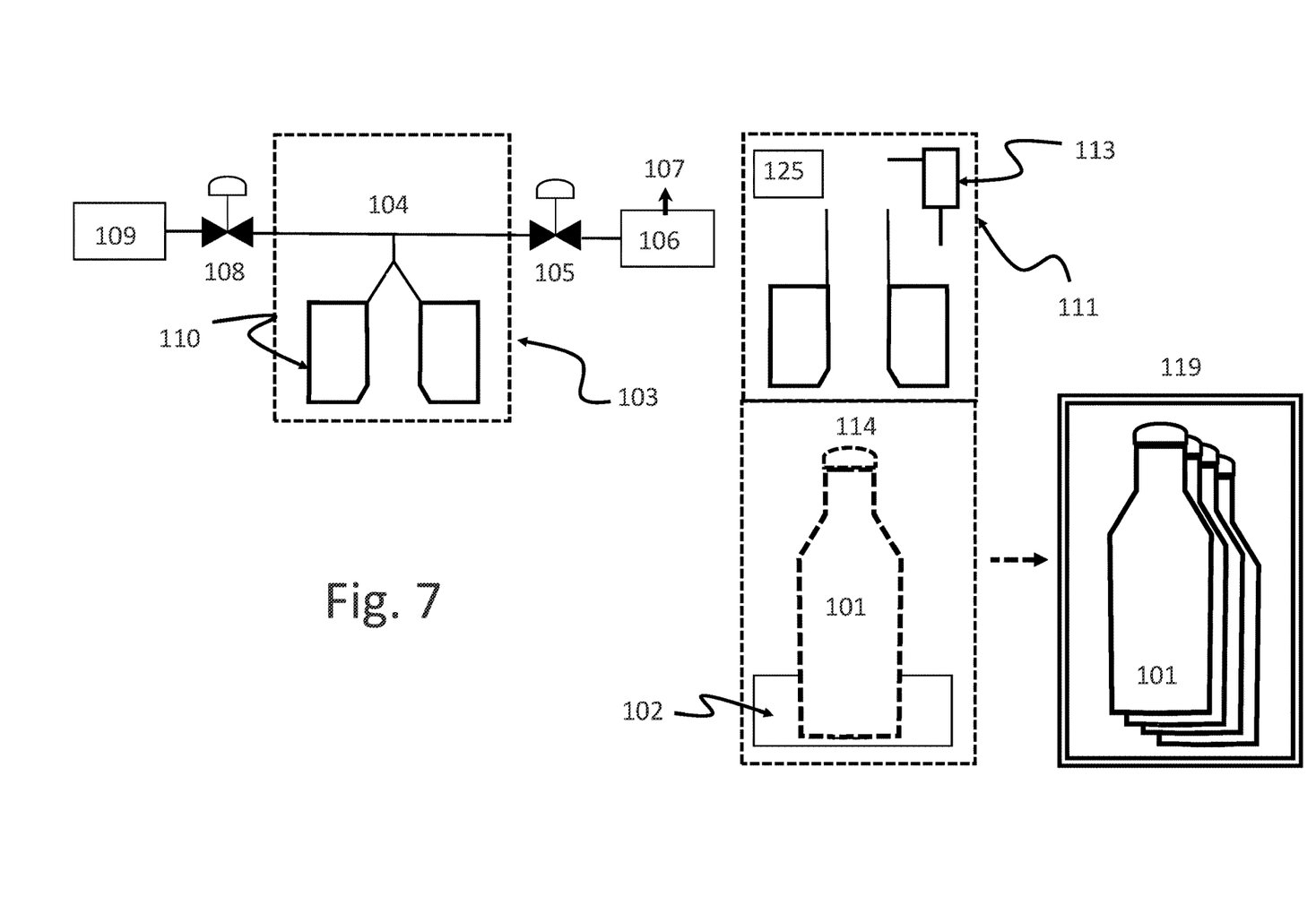
FIG. 7 is a schematic representation of the overall system during the removal phase, in accordance with one embodiment of the present invention.

Turning now to FIG. 7, cartridge 101 now exits enclosed area 103. In some embodiments, filled and capped, pressurized cartridge 101 is deposited into a safety enclosure 119, which is at approximately atmospheric pressure. This is a safety procedure in the event that here is a flaw or imperfection in the cartridge itself, the cap itself; or the weld that results in rapid decompression of the pressurized gas. Safety enclosure area may be a steel box. Multiple filled and capped cartridges 101 may be deposited into safety enclosure 119 at the same time.

Turning now to FIG. 8, after a number of filled and capped cartridges 101 have been accumulated in safety enclosure 119, the entire safety enclosure may then be heated in an oven 120 to increase the internal pressure of cartridges 101 and thus further testing the integrity of the cartridge with respect to internal pressure.

Figure 9:
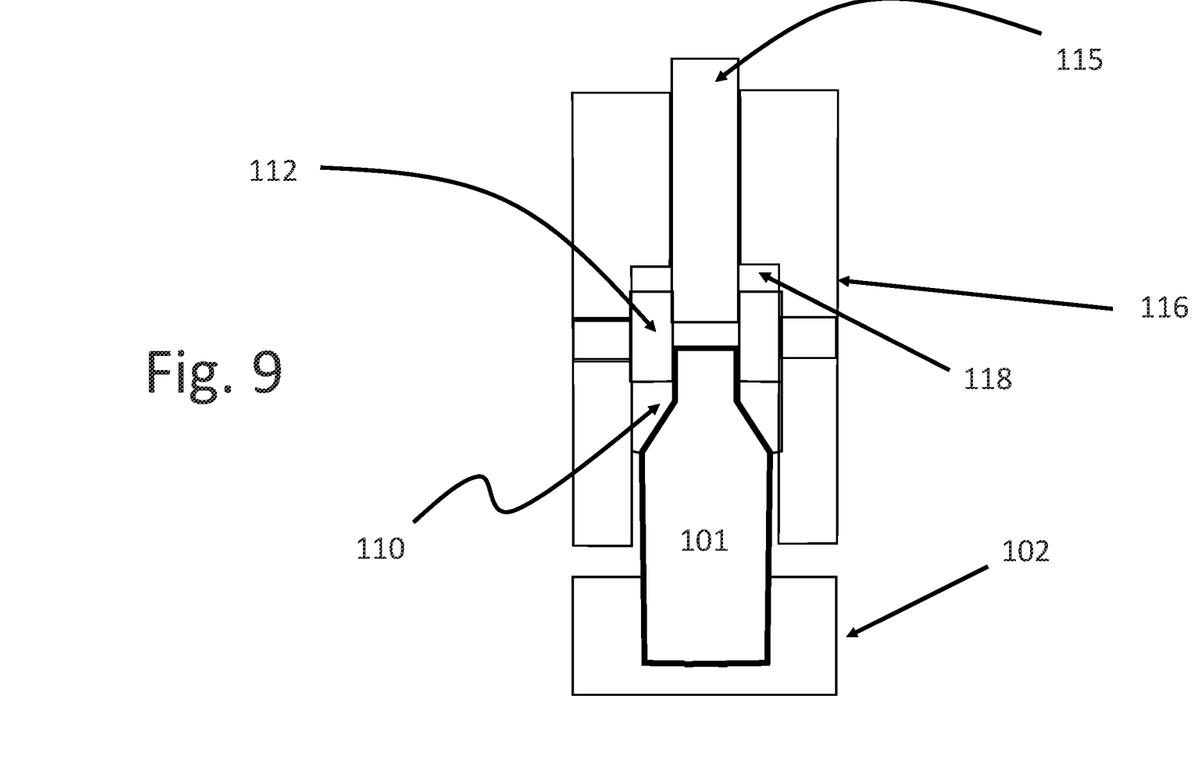
FIG. 9 is a schematic representation of another embodiment of the present invention.
Figure 10:
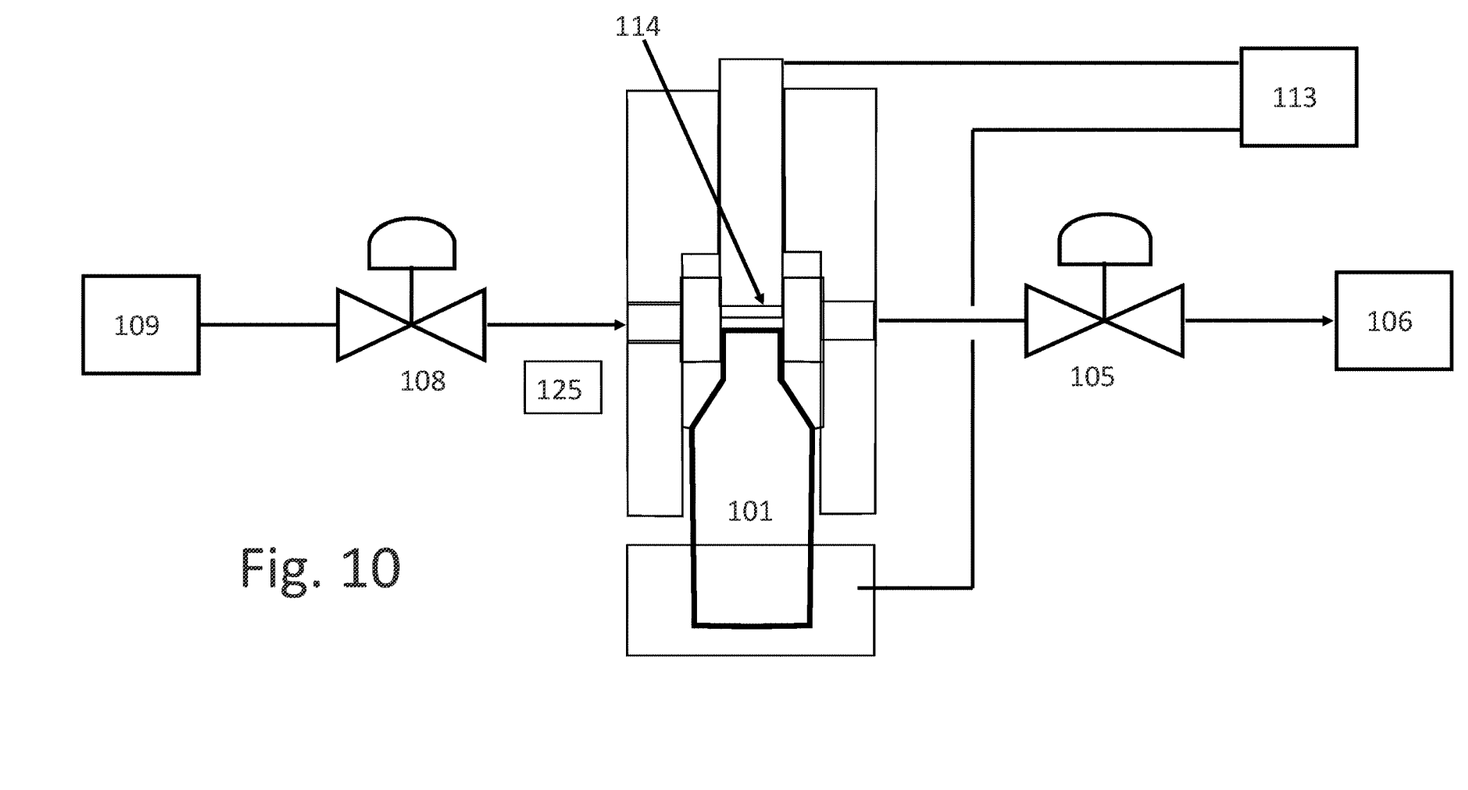
FIG. 10 is a schematic representation of another embodiment of the present invention.

Turning now to FIGS. 9 and 10, in one embodiment evacuation and filling adaptor 104 and capping and welding device 111 are contained in the same apparatus, welding and filling adaptor 116. As previously discussed, sealing member 110 is sealably attached to the top of empty and uncapped cartridge 101. Sealing member 110 may be configured to move vertically within welding and filling adapter 116, with sealing member 110 retaining the seal against cartridge 101 by means of centering member adjustment 118. Centering member adjustment may be a spring or system of springs, an elastomer, or any other means known in the art. Centering member 112, which may also move vertically within welding and filling adaptor 116, and be actuated by centering member adjustment 118, fits over the neck of cartridge 101 and thus centers and aligns cartridge 101 and the cap 114, thus ensuring a proper fit and weld.

As discussed above, with filling circuit block valve 108 closed, and evacuation circuit block valve 105 open, vacuum pump 106 is activated. Welding and filling adaptor 116 then removes the existing, residual, ambient air that is contained within cartridge 101, and thus creating at least a partial vacuum therein. Once the ambient air has been evacuated from cartridge 101, welding and filling adaptor 116 then provides medical, pharmaceutical, or pharmacopeia grade gas from source 109 at a predetermined pressure and temperature. Now, with filling circuit block valve 108 open, and evacuation circuit block valve 105 closed, medical gas from source 109 is allowed to enter cartridge 101, replacing the vacuum and pressurizing cartridge 101.

In one embodiment, the medical grade gas is carbon dioxide. The predetermined pressure and temperature of the gas determines the density of the gas, which, given the known volume of cartridge 101, allows a predetermined mass of medical gas to be present in cartridge 101. This procedure thus eliminates the need for weighing cartridge 101 either before filling, during filling, or after filling as the mass of the medical gas is known.

During the capping and welding steps sealing member 110 maintains contact with cartridge 101, thus maintaining the medical grade gas at the predetermined pressure and temperature. Welding and filling adaptor 116 includes a centering member 112 for centering cartridge 101, and a welding mechanism 113. Welding mechanism 113 include electrode 115, which is electrically isolated from the body of cartridge 101.

Welding and filling adaptor 116 firmly attaches a cap 114 to the open end of cartridge 101. Cap 114 is then permanently affixed to cartridge 101 by means of a welding mechanism 113.

These cartridges are typically referred to within the industry by a gas weight, however, this is solely based on the typical conditions (saturated at ambient temperature) of the cylinder from which they are being filled. For CO2, this is approx. 850 psia at 70° F., which results in a density of approx. 0.775 g/mL. For a 20 mL cartridge, this would result in 15.5 g of CO2. If a pump is used to fill the cartridges and/or the CO2 is cooled due to flashing inside the tubing supplying the fill system, the density can be significantly higher. This is important because the more CO2 that is filled in the cartridge, the higher the pressure will be at higher ambient temperatures. For example, a 20 mL cartridge filled with 17 g of CO2 will have a pressure of approx. 5,700 psia at 160° F. This is very close to the burst pressure of the cartridge (50 MPa; 7,250 psia).

Thus, an additional aspect is that we control the density of the CO2 by controlling its temperature and pressure so that: The fill weight of the cartridge is well controlled independent of ambient conditions. The cartridge will not exceed 4,000 psia at 160° F., providing a much higher degree of safety.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. An apparatus for filling a cartridge with medical gas, comprising a sealing mechanism configured to:
   removably seal against an open end of an uncapped and empty cartridge,
   the apparatus thereby configured to:
   evacuate the cartridge, producing at least a partial vacuum therein,
   fill the cartridge with medical gas at a predetermined pressure and temperature, and comprising a water-cooled support cradle configured to be in thermal contact with the cartridge and thereby maintain the predetermined pressure and temperature while the cartridge is capped.

2. The apparatus of claim 1, wherein the apparatus is configured to weld the cartridge after being capped.

3. The apparatus of claim 1, wherein the medical gas is medical grade, designated gas, drug approved, pharmacopeia gas or any drug related gas.

4. The apparatus of claim 1, wherein the medical gas is selected from the group consisting of oxygen, nitrogen, nitrous oxide, carbon dioxide, helium, carbon monoxide, medial air, argon, Xenon, and mixtures thereof.

5. An apparatus for filling a cartridge with medical gas, comprising:
   a sealing mechanism configured to removably seal against an open end of an uncapped and empty cartridge,
   an evacuation adapter fluidically attached to the sealing mechanism and configured to evacuate the cartridge, producing at least a partial vacuum therein,
   a fill adapter fluidically attached to the sealing mechanism and configured to fill the cartridge with medical gas at a predetermined pressure and temperature,
   a capping device fluidically attached to the sealing mechanism and configured to maintain the predetermined pressure and temperature while the cartridge is capped, and
   a water-cooled support cradle configured to be in thermal contact with the cartridge and thereby maintain the pressure and temperature of the cartridge.

6. The apparatus of claim 5, wherein the apparatus is configured to weld the cartridge after being capped.

7. The apparatus of claim 6, further comprising a welding device, wherein the evacuation adaptor, the filling adaptor, the capping device, and the welding device are located within a sealed, protective enclosure.

8. The apparatus of claim 6, further comprising a welding device, wherein the evacuation adaptor, the filling adaptor, the capping device, and the welding device are in a single apparatus.

9. The apparatus of claim 6, further comprising a welding device, wherein the welding device comprises electrical isolation between positive and negative electrodes.

10. The apparatus of claim 5, wherein the capping device further comprises a centering mechanism.

11. The apparatus of claim 5, wherein the medical gas is medical grade, designated gas, drug approved, pharmacopeia gas or any drug related gas.

12. The apparatus of claim 5, wherein the medical gas is selected from the group consisting of oxygen, nitrogen, nitrous oxide, carbon dioxide, helium, carbon monoxide, medial air, argon, Xenon, and mixtures thereof.

* * * * *